United States Patent [19]

Schmidt-Radde et al.

[11] Patent Number: 5,670,639
[45] Date of Patent: Sep. 23, 1997

[54] PREPARATION OF N-VINYLLACTAMS

[75] Inventors: Martin Schmidt-Radde, Beindersheim; Marc Heider, Neustadt; Albrecht Dams, Wachenheim; Harald Rust, Neustadt, all of Germany

[73] Assignee: BASF Aktiengesellschaft, Ludwigshafen, Germany

[21] Appl. No.: 614,682

[22] Filed: Mar. 13, 1996

[30] Foreign Application Priority Data

Mar. 15, 1995 [DE] Germany ............... 19509362.3

[51] Int. Cl.$^6$ ............ C07D 207/26; C07D 211/76; C07D 223/10
[52] U.S. Cl. ............ 540/485; 540/533; 546/243; 548/543; 548/552
[58] Field of Search .................. 548/543, 552; 546/243; 540/485, 533

[56] References Cited

U.S. PATENT DOCUMENTS 3,185,706  5/1965  Mutaffis et al. .
4,410,726  10/1983  Parthasarathy et al. .
4,873,336  10/1989  Liu et al. ............... 546/243

FOREIGN PATENT DOCUMENTS 0 512 656   11/1992  European Pat. Off. .
95983       11/1960  Netherlands .
799924      8/1958   United Kingdom .
1045627     10/1966  United Kingdom .
WO 89/09210 10/1989  WIPO .

OTHER PUBLICATIONS

Reppe et al. Liebigs Ann. Chem., vol. 601, pp. 128–138 (1956).
Nedwick, Ind. Eng. Chem. Proc., Design & Dev., vol. 1 (1962) pp. 137–141.

Primary Examiner—Mukund J. Shah
Assistant Examiner—Deepak Rao
Attorney, Agent, or Firm—John H. Shurtleff

[57] ABSTRACT

N-Vinyllactams of the general formula I

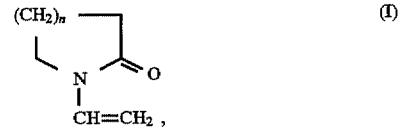

where n is from 1 to 3, are prepared by a process which comprises reaction of a lactam of the general formula II

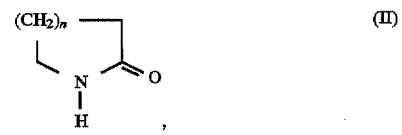

where n is from 1 to 3, with from 10 to 90 percent by weight of an aqueous alkali metal hydroxide solution with distillation at from 50° to 250° C. and from 1 to 100 mbar and with a residence time of from 0.1 to 5 hours and subsequent reaction with acetylene at from 60° to 250° C. and from 1 to 100 bar.

9 Claims, No Drawings

PREPARATION OF N-VINYLLACTAMS

The present invention relates to a process for the preparation of N-vinyllactams by distillative reaction of a lactam with an aqueous alkali metal hydroxide solution and subsequent reaction with acetylene.

Liebigs Ann. Chem. 601 (1956), 128–138, discloses the reaction of lactams and amides with acetylene in the presence of catalytic amounts of strongly basic alkali metals. By using elemental alkali metal, traces of water in the batch are avoided. Owing to difficulties in handling alkali metals, this method is not rele- vant industrially.

WO-A-89/09210 recommends the use of alkali metal salts of sterically hindered alcohols, with the result that removal of the sterically hindered alcohol formed can be dispensed with since the latter does not initiate cleavage of the lactam ring. In practice, however, this process has the disadvantage that strongly basic compounds in powder form have to be handled. These catalysts are expensive. Furthermore, the resulting alcohols are also present in the discharges from the lactam vinylation and must subsequently be separated off and disposed of.

U.S. Pat. No 3,185,706 describes the preparation of alkali metal salts of pyrrolidone for the preparation of polymers by reaction of alkali metal salts in solvents, such as alcohols, ethers or hydrocarbons bons, with pyrrolidone under reduced pressure at from 170° to 250° C.

Ind. Eng. Chem. Proc. Design & Dev. 1 (1962), 137–141, discloses that potassium hydroxide has only a short life as a catalyst for the vinylation of lactams, owing to rapid hydrolysis. The hydrolysis lysis is greatly accelerated by water. For this reason, potassium hydroxide is first added to the lactam in the reactor in this case, but this procedure is very expensive in terms of apparatus and permits only short residence times of the lactam in the reactor.

In DE-A-32 15 093, solid potassium hydroxide is used with pyrrolidone for the preparation of vinylation batches. In order to obtain good results, the water must be completely removed. The process described there is a batchwise process, and the catalyst is used in solid form, giving rise to difficulties in metering and in handling.

It is an object of the present invention to remedy the abovementioned disadvantages.

We have found that this object is achieved by a new and improved process for the preparation of N-vinyllactams of the general formula I

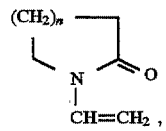

where n is from 1 to 3, which comprises reacting a lactam of the general formula II

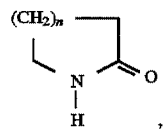

where n is from 1 to 3, with from 10 to 90 percent by weight of an aqueous alkali metal hydroxide solution with distillation at from 50° to 250° C. at from 1 to 100 mbar and with a residence time of from 0.1 to 5 hours and subsequent reaction with acetylene at from 60° to 250° C. and from 1 to 100 bar.

The novel process can be carried out as follows:

The aqueous alkali metal hydroxide solution and the lactam II can be fed, together or preferably in separate feeds, to the upper third, preferably to the upper quarter, particularly preferably to the top of the column. The pressure in the column is as a rule from 1 to 100, preferably from 1 to 30, particularly preferably from 2 to 20, mbar. Both packed columns and tray columns may be used. As a rule, these columns have at least two, ie. from 2 to 100, preferably from 2 to 10, particularly preferably from 3 to 6, theoretical plates. The column may be operated at from 50° to 250° C., preferably from 70° to 180° C. The residence time is as a rule from 0.1 to 5, preferably from 0.5 to 2, particularly preferably from 0.8 to 1.5, hours.

Suitable alkali metal hydroxide solutions are those of lithium hydroxide, sodium hydroxide, potassium hydroxide, rubidium hydroxide and cesium hydroxide, preferably of lithium hydroxide, sodium hydroxide and potassium hydroxide, particularly preferably of potassium hydroxide.

The content of alkali metal hydroxide in the aqueous solution is as a rule from 5 to 90, preferably from 30 to 60, particularly preferably from 45 to 55, in particular 50, % by weight.

While the water is generally removed via the top of the column, the vinylation batch is obtained in the bottom and is reacted with acetylene, as a rule in a separate reaction vessel at from 60° to 250° C. and from 1 to 100 bar.

This procedure is equally suitable for pyrrolidone, piperidone and caprolactam.

EXAMPLES

A) Preparation of the vinylation batches

EXAMPLES 1 to 18

500 g/hour of caprolactam and 20 g/hour of 50% KOH in water were pumped into a packed column having a nominal diameter of 43 mm and about 3 theoretical separation stages. The pressure and temperatures are shown in the table. 506 g/h of caprolactam batch were obtained at the bottom, and 14 g/h of water were obtained in the distillate.

| Example No. | Pressure [mbar] | Heating oil [°C.] | Bottom [°C.] | Top [°C.] | KOH [%] | H₂O [%] | Act. cat. [%] |
|---|---|---|---|---|---|---|---|
| 1 | 5 | 127 | 113 | 82 | 1.97 | 0.08 | 76 |
| 2 | 5 | 127 | 113 | 83 | 1.72 | 0.09 | 100 |
| 3 | 5 | 127 | 113 | 83 | 1.89 | 0.09 | 78 |
| 4 | 5 | 127 | 113 | 84 | 1.85 | 0.05 | 78 |
| 5 | 5 | 127 | 113 | 83 | 1.88 | 0.05 | 80 |
| 6 | 5 | 127 | 113 | 83 | 2.04 | 0.1 | 76 |
| 7 | 5 | 127 | 109 | 90 | 1.6 | 0.07 | 67 |
| 8 | 5 | 127 | 112 | 80 | 2.36 | 0.1 | 76 |
| 9 | 5 | 127 | 111 | 81 | 1.81 | 0.08 | 86 |
| 10 | 5 | 127 | 111 | 82 | 1.55 | 0.07 | 83 |
| 11 | 5 | 127 | 112 | 78 | 1.73 | 0.09 | 78 |
| 12 | 5 | 127 | 113 | 87 | 2 | 0.1 | 81 |
| 13 | 10 | 140 | 119 | 82 | 2.04 | 0.13 | 82 |
| 14 | 10 | 140 | 121 | 76 | 2 | 0.08 | 80 |
| 15 | 10 | 140 | 121 | 77 | 2.1 | 0.08 | 78 |
| 16 | 30 | 160 | 141 | 68 | 1.97 | 0.03 | 62.6 |
| 17 | 30 | 160 | 141 | 73 | 1.58 | 0.01 | 74.2 |
| 18 | 30 | 160 | 141 | 77 | 1.77 | 0.01 | 70.6 |

B) Reaction of the batches with acetylene

B) Reaction of the batches with acetylene

EXAMPLES I and II 150 g of a batch prepared under A) were introduced into a 300 ml high-pressure autoclave and the autoclave was flushed with 2 bar nitrogen and heated to 90° C. Acetylene was then introduced to a total pressure of 20 bar. The acetylene consumed was replaced by continuously introducing further acetylene. After the end of the reaction, the autoclave was cooled, the pressure was let down and the reaction mixture was analyzed.

| Example No. | KOH [% by weight] | Water [% by weight] | Act. cat. [%] | Life [h] | Amount of acetylene [l] | Conversion [%] | Selectivity [%] |
|---|---|---|---|---|---|---|---|
| I | 1.79 | 0.1 | 86 | 9.5 | 27.2 | 93.1 | 99 |
| II | 1.88 | 0.05 | 80 | 11.5 | 25.7 | 91.8 | 100 |

We claim:

1. A process for the preparation of an N-vinyllactam of the formula I

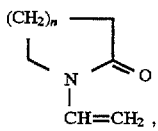

where n is from 1 to 3, which comprises reacting a lactam of the formula II

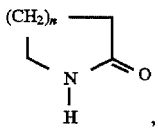

where n is from 1 to 3, with from 10 to 90 percent by weight of an aqueous alkali metal hydroxide solution with distillation at from 50° to 250° C. and from 1 to 100 mbar and with a residence time of from 0.1 to 5 hours and subsequent reaction with acetylene at from 60° to 250° C. and from 1 to 100 bar.

2. A process for the preparation of an N-vinyllactam as claimed in claim 1, wherein the distillative reaction is carried out in a column having at least 2 theoretical plates.

3. A process for the preparation of an N-vinyllactam as claimed in claim 1, wherein the lactam II and the aqueous alkali metal hydroxide solution are fed into the upper third of the column during the distillative reaction.

4. A process for the preparation of an N-vinyllactam as claimed in claim 1, wherein the distillative reaction is carried out at from 70° to 180° C.

5. A process for the preparation of an N-vinyllactam as claimed in claim 1, wherein the distillative reaction is carried out at from 1 to 30 mbar.

6. A process for the preparation of an N-vinyllactam as claimed in claim 1, wherein the distillative reaction is carried out with a residence time of from 0.5 to 2 hours.

7. A process for the preparation of an N-vinyllactam as claimed in claim 1, wherein the reaction is carried out using from 30 to 60 % by weight of an aqueous alkali metal hydroxide solution.

8. A process for the preparation of an N-vinyllactam as claimed in claim 1, wherein the reaction is carried out using from 45 to 55% by weight of an aqueous alkali metal hydroxide solution.

9. A process for the preparation of an N-vinyllactam as claimed in claim 1, wherein the aqueous alkali metal hydroxide solution used is aqueous potassium hydroxide solution.

* * * * *